(12) United States Patent
Keller

(10) Patent No.: US 7,320,689 B2
(45) Date of Patent: *Jan. 22, 2008

(54) MULTI-PART CERVICAL ENDOPROSTHESIS WITH INSERTION INSTRUMENT

(75) Inventor: Arnold Keller, Kayhude (DE)

(73) Assignee: Cervitech, Inc., Rockaway, NJ (US)

( * ) Notice: Subject to any disclaimer, the term of this patent is extended or adjusted under 35 U.S.C. 154(b) by 86 days.

This patent is subject to a terminal disclaimer.

(21) Appl. No.: 10/619,179

(22) Filed: Jul. 15, 2003

(65) Prior Publication Data

US 2005/0015094 A1 Jan. 20, 2005

(51) Int. Cl.
*A61B 17/58* (2006.01)
*A61F 2/00* (2006.01)
*A61F 2/44* (2006.01)

(52) U.S. Cl. ...................................... 606/99; 623/17.16
(58) Field of Classification Search ................ 606/53, 606/60, 61, 86, 99; 623/11.11, 16.11, 17.11–17.16
See application file for complete search history.

(56) References Cited

U.S. PATENT DOCUMENTS

| 3,960,147 A | | 6/1976 | Murray | |
|---|---|---|---|---|
| 4,759,766 A | | 7/1988 | Buettner-Janz et al. | |
| 4,997,432 A | * | 3/1991 | Keller | ........................ 606/61 |
| 5,314,477 A | * | 5/1994 | Marnay | .................... 623/17.15 |
| 5,431,658 A | | 7/1995 | Moskovich | |
| 5,556,431 A | * | 9/1996 | Buttner-Janz | ............ 623/17.15 |
| 5,720,751 A | | 2/1998 | Jackson | |
| 6,368,350 B1 | | 4/2002 | Erickson et al. | |
| 6,402,785 B1 | * | 6/2002 | Zdeblick et al. | .......... 623/17.16 |
| 6,478,800 B1 | * | 11/2002 | Fraser et al. | ................... 606/99 |
| 6,517,580 B1 | * | 2/2003 | Ramadan et al. | ......... 623/17.15 |
| 6,755,841 B2 | * | 6/2004 | Fraser et al. | ................... 606/99 |
| 6,981,990 B2 | * | 1/2006 | Keller | ...................... 623/17.11 |
| 7,118,580 B1 | * | 10/2006 | Beyersdorff et al. | ........... 606/99 |
| 2002/0072752 A1 | | 6/2002 | Zucherman et al. | |
| 2003/0069586 A1 | * | 4/2003 | Errico et al. | ................... 606/99 |
| 2003/0083747 A1 | * | 5/2003 | Winterbottom et al. | ... 623/17.11 |

FOREIGN PATENT DOCUMENTS

EP  1 306 064 A1  5/2003
WO  WO 01/19295 A1  3/2001

* cited by examiner

*Primary Examiner*—Anuradha Ramana
(74) *Attorney, Agent, or Firm*—Morrison & Foerster LLP

(57) ABSTRACT

A multi-part intervertebral endoprosthesis includes a top closure plate, a bottom closure plate, a sliding core between the closure plates, each closure plate having a pair of receiving openings or projections, and an insertion instrument which has a handgrip area and a gripping area with retention projections or openings which, in order to hold the intervertebral endoprosthesis on the insertion instrument, can be engaged in the receiving openings or projections. The receiving openings are arranged in lateral side faces of the intervertebral endoprosthesis, and at least the pair of receiving openings on one of the closure plates has an extended shape extending in the direction toward the other closure plate. In this way, without making changes to the insertion instrument, intervertebral endoprostheses with sliding cores of different thicknesses can be held securely and with the guarantee that they are correct positioned within the insertion instrument.

17 Claims, 3 Drawing Sheets

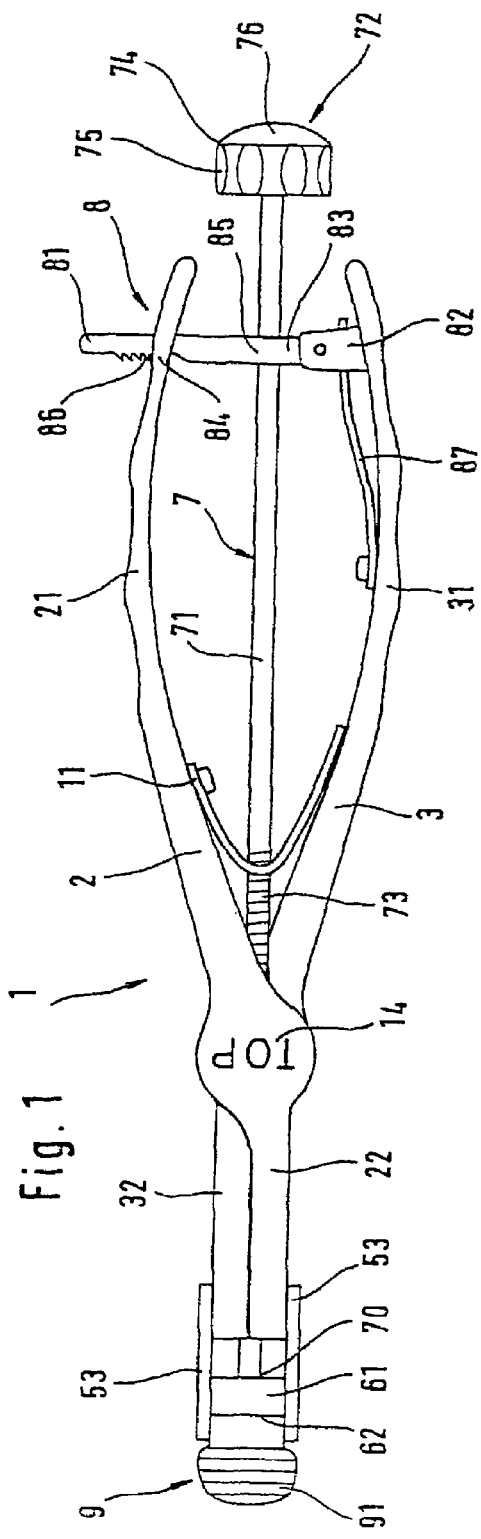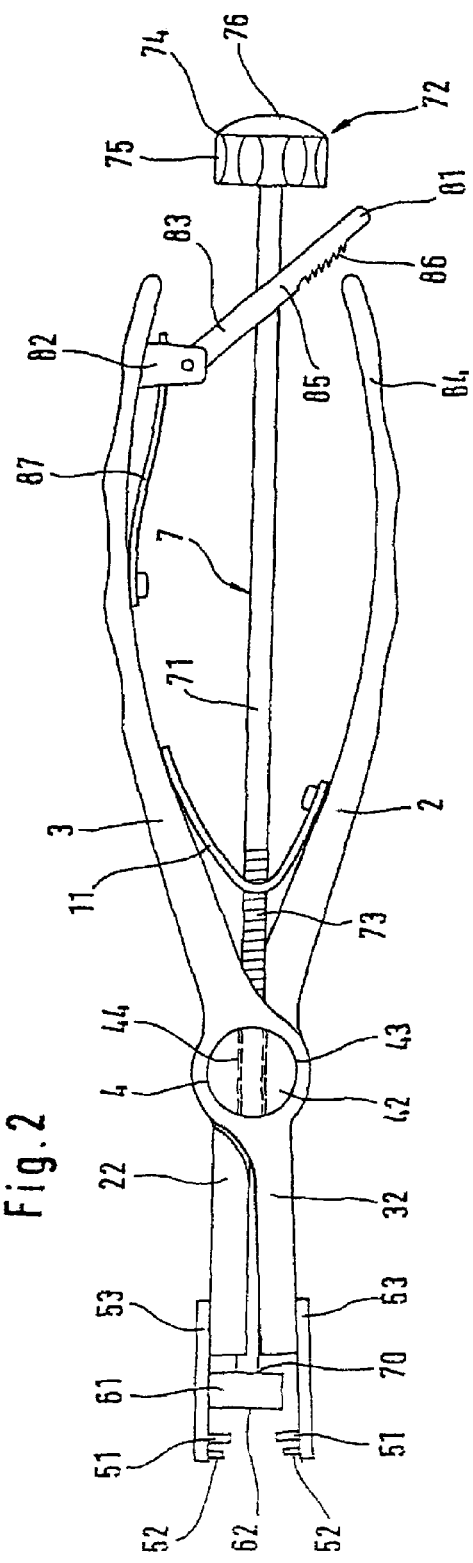

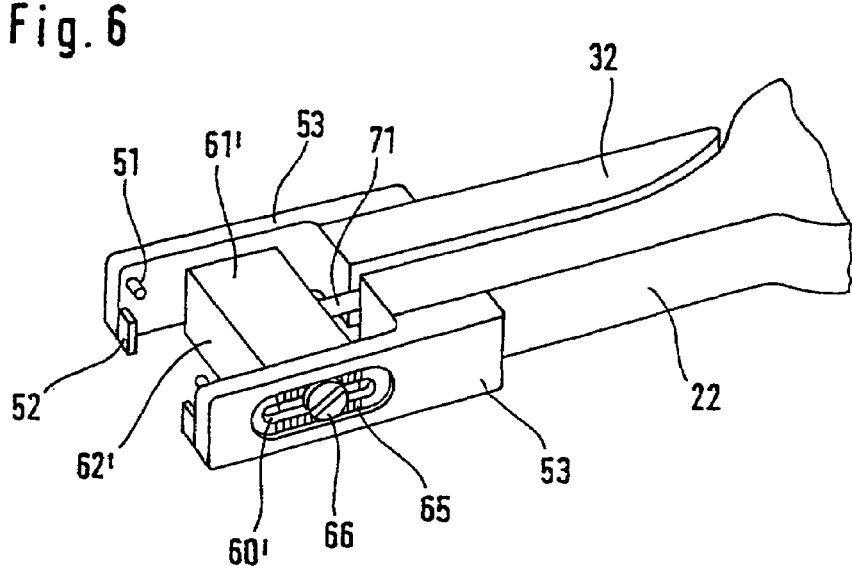
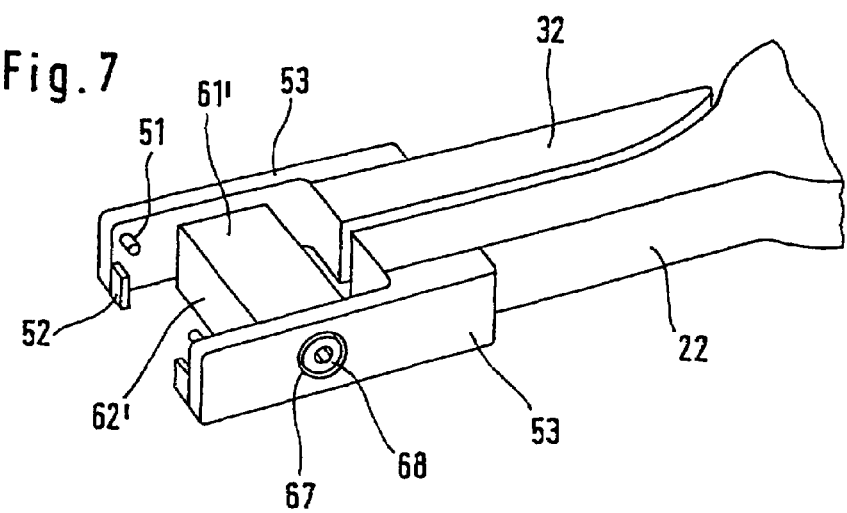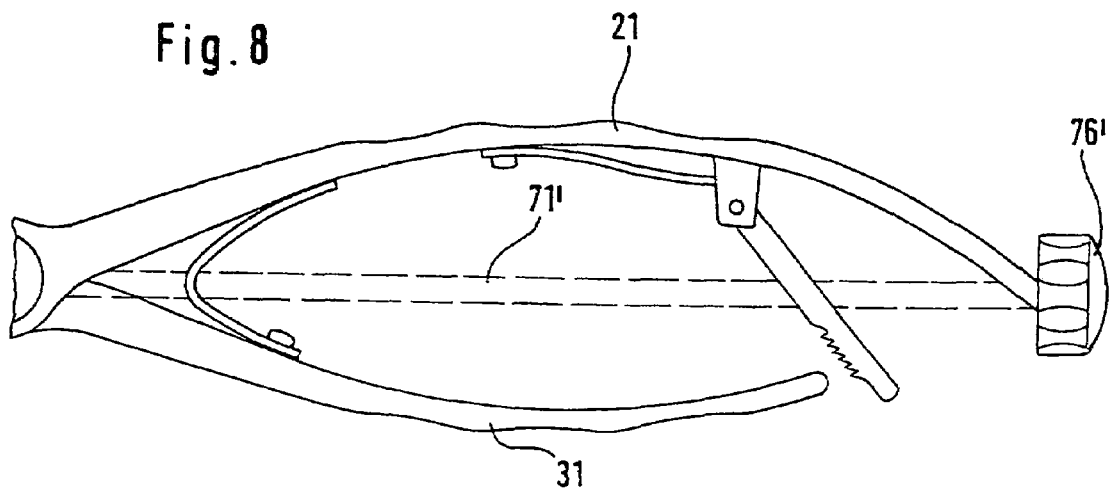

MULTI-PART CERVICAL ENDOPROSTHESIS WITH INSERTION INSTRUMENT

FIELD OF THE INVENTION

The invention relates to an arrangement of a multi-part intervertebral endoprosthesis, which has a top closure plate and bottom closure plate and, between these, a sliding core, each closure plate being assigned a pair of receiving openings or projections, and of an insertion instrument, which has a handgrip area and a gripping area with retention projections or openings which, in order to hold the intervertebral endoprosthesis on the insertion instrument, can be engaged in the receiving openings or projections.

BACKGROUND OF THE INVENTION

To implant intervertebral prostheses, special insertion instruments are needed because of the difficult access. In order to ensure that the intervertebral prosthesis can be held by the insertion instrument, it is known to provide bores on the ventral end face of the closure plates, which bores point in the direction of insertion and into which correspondingly shaped pins on the insertion instrument engage (U.S. Pat. No. 5,314,477 and WO-A-0119295). Although this type of securing is quite safe, the space needed for the bores means that it is not possible to reduce the size of the end face and thus of the overall closure plate. This design is not really suitable for use in confined conditions.

In another known intervertebral prosthesis system (EP-A-1 306 064), no bores are provided, and instead the insertion instrument has two pairs of gripping members which are connected rigidly to one another and which in each case hold a closure plate between them by friction. For very small implants, of the kind which are used in the area of the cervical spine and which have to be positioned very precisely, this may be too unreliable.

The object of the invention is to make available an improved arrangement of intervertebral endoprosthesis and insertion instrument which is adapted in particular to the requirements of implantation in confined conditions, as apply in particular in the area of the cervical spine.

SUMMARY OF THE INVENTION

The solution according to the invention lies in a multi-part intervertebral endoprosthesis as disclosed herein that includes a top closure plate, a bottom closure plate, a sliding core between the top and bottom closure plates and an insertion instrument. Each closure plate includes a pair of receiving openings or projections, and the insertion instrument includes a handgrip and a gripping portion for engaging the top and bottom closure plates with corresponding retention projections or openings which, in order to hold the intervertebral endoprosthesis on the insertion instrument, are configured to engage in the corresponding receiving openings or projections. The receiving openings are arranged in lateral side faces of the closure plates relative to the implanted position of the closure plates, and the pair of receiving openings assigned to at least one of the closure plates has an extended shape extending in a direction toward the other closure plate. Advantageous developments are the subject of the more detailed embodiments disclosed below.

In the case of an arrangement of a multi-part intervertebral endoprosthesis, which has a top closure plate and bottom closure plate and, between these, a sliding core, each closure plate being assigned a pair of receiving openings or projections, and of an insertion instrument, which has a handgrip area and a gripping area with retention projections or openings which, in order to hold the intervertebral endoprosthesis on the insertion instrument, can be engaged in the receiving openings or projections, the invention provides that the receiving openings are arranged in lateral side faces of the intervertebral endoprosthesis, and at least the pair of receiving openings assigned to one of the closure plates has a shape extended in the direction toward the other closure plate.

A shape extended in the direction toward the other closure plate is understood to mean that the receiving opening leaves space free, for a retention projection engaging in it, in one direction, namely toward the other closure plate, so that the retention projection, viewed in this direction, can assume different positions. It could also be said that the closure plate is designed as an oblong hole, the longitudinal axis of the oblong hole pointing toward the other closure plate. An expedient embodiment of a receiving opening designed in this way is a slit.

With this design of the receiving openings, the arrangement according to the invention makes it possible to grip and to insert intervertebral endoprostheses with sliding cores of different thicknesses without having to make adjustments or changes for this purpose. If, during an operation, it transpires that the proposed intervertebral endoprosthesis does not fit, the surgeon can therefore choose another one of different height from a set of instruments and simply place it in and insert it with the insertion instrument. This is a considerable advantage especially in the case of small intervertebral endoprostheses, for example for the cervical spine, which because of their smallness permit only minimal tolerances during implantation.

Arranging the receiving openings (or projections) on the lateral side faces, instead of on the front face of the closure plates, as is the case in the prior art, reduces the amount of space required. It permits a smaller and more space-saving design of the intervertebral endoprosthesis. The arrangement on the lateral side faces has the further advantage that the retention projections are arranged transversely with respect to the direction of insertion, and thus the force transmission upon insertion of the intervertebral endoprosthesis takes place with a form-fit. By virtue of this design, the intervertebral endoprosthesis is on the one hand held securely on the insertion instrument while on the other hand it can be easily separated from the insertion instrument by release of the form-fit. In the prior art, this is not the case. There, the fact that the retention projections point in the direction of insertion means that the force transmission is effected by frictional fit. This results in unreliable positioning and undesirably high release forces for overcoming the frictional fit. The invention thus permits easier handling and more precise positioning, which is especially important when space is limited.

The receiving opening with an extended shape preferably extends over the entire height of the assigned closure plate. This permits a compensation for different heights over a greater range. The receiving opening with an extended shape can, however, also be arranged on the sliding core or on both. In the latter case, it is important that they are flush with one another. It can extend over part of the height or preferably the entire height of the sliding core.

It can be expedient for the shape of the receiving opening to be chosen such that it narrows with increasing depth. This facilitates insertion of the corresponding retention projection while nevertheless ensuring a firm fit so that only a small amount of play, if any, exists.

The pair of receiving openings assigned to the other closure plate preferably has a concentrated shape. Unlike the case with the extended shape, in the case of a concentrated shape no free space is available for the engaging retention projection, i.e. the retention projection can assume only one position. This receiving opening is expediently designed as a round bore. This ensures that the intervertebral endoprosthesis assumes a defined position in relation to the retention projection engaging therein and thus also in relation to the insertion instrument. Differences in the dimensions of the intervertebral endoprosthesis, whether as a result of different heights of the sliding core or because of production tolerances, can be taken up by virtue of the configuration, according to the invention, of the receiving opening with the extended shape. Thus, despite possible differences, the intervertebral endoprosthesis can be held in a defined manner. A different configuration of the two pairs of receiving openings also has the advantage of providing a guarantee against mix-ups. Thus, the intervertebral endoprosthesis can be held on the insertion instrument only with the correct orientation; an incorrect arrangement is avoided in this way.

In general, the receiving openings are arranged on the intervertebral endoprosthesis and the retention projections are arranged on the insertion instrument. This is a tried and tested arrangement. However, the invention is not limited to this, and instead provision can also be made for the projections to be arranged on the intervertebral endoprosthesis and for the openings to be arranged on the insertion instrument.

It is particularly advantageous, for the intervertebral endoprosthesis, to provide different sizes with sliding cores of different thicknesses. Thus, depending on the anatomical requirements, the correct intervertebral endoprosthesis can be selected and implanted with the insertion instrument, without changes having to be made to the insertion instrument. If, during an operation, the surgeon realizes that the intervertebral endoprosthesis originally chosen is too high or too low, he simply has to select another intervertebral endoprosthesis with a suitable height and can insert this without difficulty.

The insertion instrument is advantageously designed as a forceps. The retention projections can be arranged on the inside faces of the jaw parts. In this way it is possible, by simply closing the forceps, to introduce the retention projections into the receiving openings and thus hold the intervertebral endoprosthesis on the forceps. Moreover, the design as forceps also permits a space-saving construction. This affords considerable advantages in terms of handling, especially under confined conditions, as in the area of the cervical spine. In addition, the forceps-like design has the advantage that different widths of the intervertebral endoprosthesis can be easily compensated by it. This is done by closing the forceps to a greater or lesser extent depending on the width of the intervertebral endoprosthesis. In combination with the configuration, according to the invention, of the receiving openings, it is thus possible to compensate for different widths and also different thicknesses of the intervertebral endoprosthesis. This gives the arrangement a high degree of versatility.

The retention projections are preferably designed as small plates and as pins. Retention projections designed in this way permit good adaptation to the shape of the receiving openings and thus ensure that the intervertebral endoprosthesis sits securely, and with little play, on the insertion instrument.

It is expedient for a block with an abutment surface for bearing on the intervertebral endoprosthesis to be provided on a gripping area. When the intervertebral endoprosthesis is received by the insertion instrument, the retention projections engage in the receiving openings (or vice versa) and have the effect that the intervertebral endoprosthesis assumes a defined position with respect to the insertion instrument. The block is arranged so that its abutment surface bears on the intervertebral endoprosthesis. The forces needed for inserting the intervertebral endoprosthesis can then be applied to the intervertebral endoprosthesis via the abutment surface, and the retention projections do not have to take up these forces acting in the direction of insertion. They can be of fairly small dimension and therefore made very fine, as is desired for precise positioning, without having to take into consideration the high force transmission when striking the intervertebral endoprosthesis home. In addition, the block has the advantageous effect of ensuring that the intervertebral endoprosthesis does not turn and that its elements do not open. The intervertebral endoprosthesis can thus be inserted safely, easily and with precise positioning.

The block can be arranged to be movable in the longitudinal direction by means of an actuating device. However, it can also be arranged rigidly on the gripping area. Rigidly is to be understood here as meaning that the block is not moved while the insertion instrument is being used for holding and inserting; it is not intended to mean that it cannot be moved for adjustment purposes, for example for adaptation to another prosthesis size. This can be achieved, for example, by securing it by means of a clamping screw. It is preferable, however, for the block to be secured on the gripping area by means of a through-screw.

A rod with a handle in the rear area of the handgrip part is expediently arranged on the block. It simplifies the application of the insertion force to the insertion instrument and to the intervertebral endoprosthesis. For this purpose, the handle is preferably designed as a strike head.

It is expedient to arrange the rigid block on the jaw insert. Adaptation to different intervertebral endoprostheses can then be carried out simply by exchanging the jaw insert.

BRIEF DESCRIPTION OF THE DRAWINGS

The invention is explained below with reference to the drawing in which an advantageous illustrative embodiment is shown, and where:

FIG. 1 shows an overall view of the arrangement according to the invention, seen from above;

FIG. 2 shows an overall view of the insertion instrument, seen from below;

FIG. 6 shows an enlarged detail view of a jaw part in another embodiment of the insertion instrument;

FIG. 7 shows an enlarged detail view of a jaw part in a further embodiment of the insertion instrument; and FIG. 8 shows a detail view of a handgrip part of the insertion instrument according to FIG. 7.

DETAILED DESCRIPTION OF THE INVENTION

Figure 4:
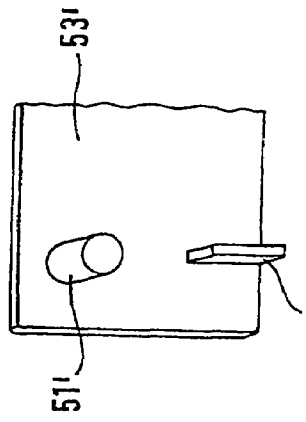
FIG. 4 shows a detail view of another jaw insert.
Figure 3:
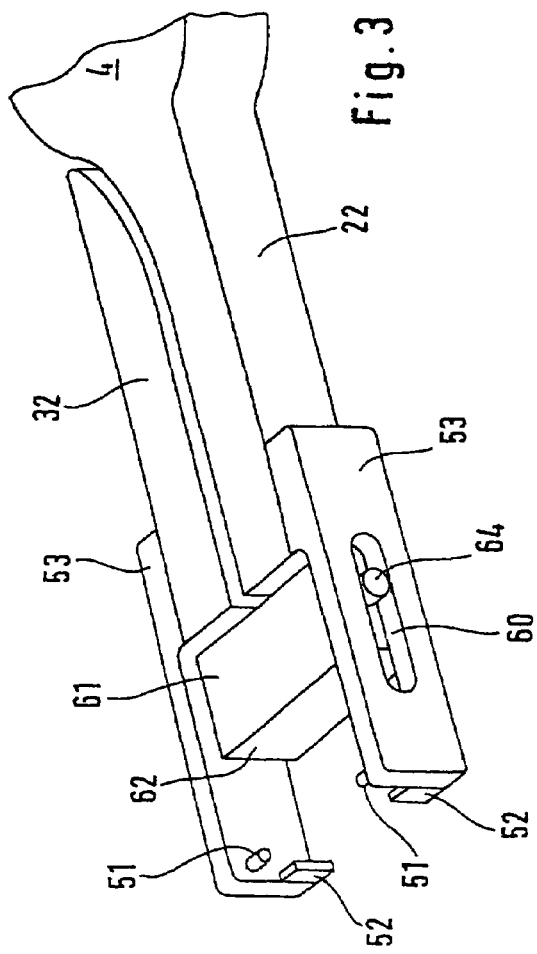
FIG. 3 shows an enlarged detail view of a jaw part of the insertion instrument, in a longitudinal axis section.

The illustrative embodiment shown is an insertion instrument designed as a forceps (labeled as a whole by reference number 1) and a cervical prosthesis 9 as intervertebral endoprosthesis. It is intended for implantation in the space between two adjacent vertebral bodies of the cervical spine (not shown).

The cervical prosthesis 9 consists of a top closure plate 91 and of a bottom closure plate 92, with a sliding core 93 arranged between these. The cervical prosthesis 9 is intended for implantation in the space between two adjacent vertebrae of the human spinal column. The top closure plate 91 is secured to the lower face of the upper vertebra and the bottom closure plate 92 is secured to the upper face of the lower vertebra. To ensure that the cervical prosthesis 9 for insertion can be received securely by the forceps 1, the top and bottom closure plates 91, 92 are provided with receiving openings. They are situated in the front area of the closure plates, in the area of a ventral securing flange 94, 95. The receiving opening assigned to the top closure plate 91 is designed as a round bore 97 with a countersink. The receiving opening assigned to the bottom closure plate 92 is designed as a slit 96 on the side flank of the bottom closure plate 92 itself and as a slit 96' formed in the side flank of the sliding core 93. The slits 96 and 96' are flush, so that they form a continuous channel. It is not absolutely essential that the slit 96, 96' is formed both in the bottom closure plate 92 and also in the sliding core 93; it may also be sufficient to provide it only in one of the two.

The forceps 1 is made up of two forceps halves 2, 3 which are connected to one another movably via a pivot hinge 4. In their rear area, the forceps halves 2, 3 have a respective handgrip part 21, 31 and in their front area they have a respective jaw part 22, 32. The pivot hinge 4 is arranged at the transition between the handgrip parts 21, 31 and the jaw parts 22, 32. It is formed by a pin 42 on the forceps half 2 (in FIG. 1 it extends upward from the plane of the drawing), which pin 42 is mounted in a matching opening 43 in the central area of the other forceps half 3. The bearing pin 42 has a through-bore 44 which runs from the handgrip area of the forceps halves 2, 3 to the jaw area. It will be discussed in more detail later. The pivot hinge 4 allows the handgrip parts 21, 31 of the forceps halves 2, 3 to be moved toward one another so that the jaw parts 22, 32 close, and vice versa.

The jaw parts 22, 32 function as gripping members. In the front area, on their mutually facing inner surfaces, they each have two projections 51, 52 pointing in the tensioning direction 12. These projections are not arranged directly on the jaw parts 22, 32, but instead on jaw inserts 53 which are secured exchangeably, by means of a screw (not shown), in a corresponding recess on the outer surfaces of the jaw parts 22, 32. Each jaw insert 53 has a projection 51 and a projection 52. The projection 51 is formed like a pin and is located in the upper area of the jaw insert 53, while the projection 52 is formed like a small plate and is situated in the lower area of the jaw insert 53. The dimensions and arrangement of the projections 51, 52 are adapted to corresponding receiving openings on the cervical prostheses 9 to be received. This will be explained in more detail later.

The round bore 97 is dimensioned so as to match a pin-like projection 51 on the forceps 1. By means of the countersink, the pin-like projection 51 can be easily introduced into the round bore 97. The slit 96, 96' has an elongate shape in the direction toward the top closure plate 91. The projection 52 formed like a small plate and arranged on the forceps 1 is adapted in terms of its breadth to the width of the slit 96, 96', so that it is guided along the slit. In this way, the relative position of the cervical prosthesis 9 in relation to the forceps 1 is fixed by the pin-like projection 51 engaging in the round bore 97, while the projection 52 in the form of a small plate engages at different points in the slit 96, 96', depending on the thickness of the sliding core 93, and thus permits compensation for different sliding cores 93. FIG. 5a shows a cervical prosthesis of medium thickness and the front area of the forceps 1 with the projections 51 and 52. When the cervical prosthesis 9 is received by the forceps 1, the pin-like projection 51 engages in the round bore 97 and fixes the cervical prosthesis against displacement. The projection 52 formed like a small plate engages in the slit 96 of the bottom closure plate 92 and in the immediately adjoining lower area of the slit 96' of the sliding core 93. For comparison, FIG. 5b shows a cervical prosthesis 9' with a thicker sliding core 93'. Once again, the pin-like projection 51 engages in the receiving bore 97. However, because of the thicker sliding core 93', the projection 52 formed like a small plate no longer engages in the slit 96 of the bottom closure plate 92, but only in the slit 96' of the sliding core 93'. In this way, despite its different height, the cervical prosthesis 9' is likewise held securely in a defined position on the forceps 1.

Arranged on the jaw part 22 there is a guide rail 60 which holds a block 61 such that the latter is longitudinally displaceable in the forward and rearward direction on the forceps half 2. The guide rail 60 is designed as an oblong hole in the jaw insert 53 of the jaw part 22. A grub screw arranged laterally in the block 61 engages in the oblong hole forming the guide rail 60 and guides the block 61 in the longitudinal direction. Instead of the oblong hole, other guide elements can also be provided which allow the block 61 to be guided in forward and rearward movement in the longitudinal direction, for example a dovetail guide. At its front end, the block 61 is provided with an abutment surface 62 designed to cooperate with the cervical prosthesis 9.

The block 61 is engaged by an actuating device 7 which extends from the rear area of the block 61 via the through-bore 44 and into the area between the handgrip parts 21, 31. The actuating device 7 comprises a coupling element 70 for connection to the block 61, which, in the illustrative embodiment shown, is a vertebral support suitable for transmitting shear forces, and it moreover comprises a rod 71 and a handle 72 for actuation. Provided in the front area of the rod 71 there is an external thread 73 which cooperates with a complementary internal thread (not shown) in the through-bore 44 of the pin 42 as an instrument-fixed guide. By turning the handle 72, it is thus possible for the rod 71, and with it the block 61 via the coupling element 70, to be moved backward and forward along the guide rail 60. The handle 72 is designed as a rotatable knob which, on its outer circumference 74, has a suitable surface finish, for example a coarse ribbing 75, to allow the operating surgeon a good grip.

The rear end of the handle 72 is provided with a convex bulge 76. It serves as a strike head for the actuating device 7. Impulses of strikes acting on the bulge 76 of the strike head are transmitted by this via the rod 71 of the actuating device 7, the shear-resistant vertebral support 70 and the block 61, to the latter's abutment surface 62.

Instead of the longitudinally movable block 61, it is alternatively possible to provide a block 61' which is arranged rigidly on the forceps half 2 and which is arranged such that its abutment surface 62' bears on the held cervical prosthesis 9. This is especially of interest when the cervical prostheses 9 used, although being able to differ in terms of their height and/or width, nevertheless have identical length dimensions. Since, because of the configuration, according to the invention, of the receiving openings 96, 97 and retention projections 51, 52, the cervical prosthesis 9 can be held in a defined position on the forceps 1, a longitudinal mobility of the block is not absolutely essential. By virtue of the defined position, it is also possible, with a rigid block 61', for it to bear with its abutment surface 62' on the cervical prosthesis 9. The insertion forces, in particular the striking forces, can therefore be transmitted as reliably and safely as in the embodiment with a movable block. It goes without saying that, in the case of the rigidly arranged block 61', a guide 60 is unnecessary. However, it can also be retained, in which case the block 61' can be secured by means of a clamping screw 66 (FIG. 6). For better securing, the oblong hole 60 is provided with ribbing 65 for the clamping screw 66. It is simpler to secure the rigid block 61' to the grip part by means of welding or screwing to the grip part 22 or its jaw insert 53. In the latter case, a screw 68 is preferably recessed in a bore 67 of the jaw insert 53 (see FIG. 7). Since the actuating device 7 no longer has to effect any longitudinal displacement, it is possible to dispense with the external thread 73 on the rod 71 and the counterthread in the through-bore 44; the through-bore 44 functions only as a guide for the rod 71. The shear-resistant vertebral support 70 also does not have to transmit any rotation movement and can be replaced by a rigid, shear-resistant connection, e.g. by a screw or weld arrangement. The handle 72 continues to function as a strike head and for this purpose preferably has the bulge 76. By dispensing with the longitudinally movable arrangement of the block 61' and by omitting the actuating device for moving the block, this embodiment is less expensive to produce and easier to use.

In another embodiment, provision is made, for the purpose of further simplification, for the rear end of the handgrip part 21 to be designed as a strike head and to be provided with a bulge 76'. If appropriate, a reinforcement rod 71' can be provided which connects the rear end of the handgrip part 21 to its front end.

In the embodiments with a rigid block 61', the impulses are transmitted from the bulge 76, 76' to the block 61' and its abutment surface 62' via the rod 71, 71' and the forceps half 2.

A locking device 8 for the handgrip parts 21, 31 is provided in the rear area of the forceps 1. This locking device 8 comprises a pivotably movable catch element 83 and a locking pawl 84 (which are arranged opposite one another on the handgrip parts 21, 31), a release device 81, a base 82 and a spring 87. The rear end of the handgrip part 21 is designed as a fork, the locking pawl 84 being formed by a beveling of the base of the fork. The catch element 83 is mounted by the base 82 in the plane spanned by the handgrip parts 21, 31. The spring 87 is designed as a leaf spring and acts on that end of the catch element 83 mounted in the base 82 in such a way that it is pressed forward to the locking pawl 84. Starting from the base 82, the catch element 83 has a wide area and a narrow area. In its narrow area, the catch element 83 has, on its front face, a toothing 86 into which, when the forceps 1 is closed, the locking pawl 84 engages and locks it, so that the handgrip parts 21, 31 cannot move away from another and, as a result, the insertion instrument 1 is safeguarded against inadvertently springing open. In this way, it is possible for even substantial loads, for example hammer strikes, to be applied to the bulge 76 on the forceps 1 without any fear of inadvertent opening and without the operating surgeon needing to secure the handgrip parts 21, 31 by manual force against undesired opening. To open the forceps 1 after implantation has been carried out, the catch element 83 is pivoted rearward by applying rearward pressure on the release element 81, by which means the locking pawl 84 is freed from the catch element 83, and the handgrip parts 21, 31 thus move apart from one another under the action of the spring 11. With the forceps 1 in the opened state, the catch element 83 is pivoted rearward counter to the force of the spring 87. Provided in the wide area of the catch element 83 there is a guide 85 which is designed as an oblong hole and which is used to hold the rod 71, even when the forceps 1 is open, in a defined position in the longitudinal axis 10 and to avoid deflection of the rod 71 even under high loads.

Also fixed on the handgrip part 31 there is a leaf spring 11 which is guided round the rod 71 to the other handgrip part 21. With the forceps 1 closed, this leaf spring 11 is tensioned and has the effect that, after release of the catch element 83, the insertion instrument 1 automatically opens to permit removal.

The cooperation with the cervical prosthesis 9 will be described now. To receive the cervical prosthesis 9 with the forceps 1, the cervical prosthesis 9 is brought into the area between the jaw parts 22, 32 and the forceps 1 is closed, as a result of which the jaw parts 22, 32 move toward one another. In so doing, the projections 51, 52 engage in the corresponding receiving openings of the two closure plates 91, 92, the pins 51 engaging in the bore 97 and the small plates 52 engaging in the slits 96, 96'. In this way, the cervical prosthesis 9, in the tensioning direction, is held free from play on the forceps 1. The different design of the projections 51, 52 and of the receiving openings configured as bores 97 and slits 96 ensures that the cervical prosthesis 9 can be held on the forceps 1 only with the correct orientation. If, as in the illustrated embodiment, the forceps 1 is additionally provided with a marking 14 for the top, this in practice eliminates the possibility of incorrect implantation as a result of incorrect orientation of the cervical prosthesis 9. After the cervical prosthesis 9 has in this way been received in the correct orientation on the forceps 1, the rod. 71 can be moved forward via the actuating device 7 by turning the handle 72, with the result that the block 61 comes to lie from the rear with its abutment surface 62 on the flange 94, 95 of the cervical prosthesis 9. In doing so, the block 61 tensions the cervical prosthesis 9 against the projections 51, 52 and thus orients the cervical prosthesis 9 in a defined position. Any play existing in the longitudinal axis direction between the projections 51, 52 and the bores 97 and the slits 96 is compensated in this way. The cervical prosthesis 9 is thus held securely and in a precise position on the insertion instrument 1. In addition, the fact that the block 61 bears on the flanges 93, 94 of the two closure plates 91, 92 ensures that the two closure plates 91, 92 move away from one another at their front end. This eliminates the possibility of the cervical prosthesis 9 opening, which would prevent successful introduction into the intervertebral space.

Figure 5:
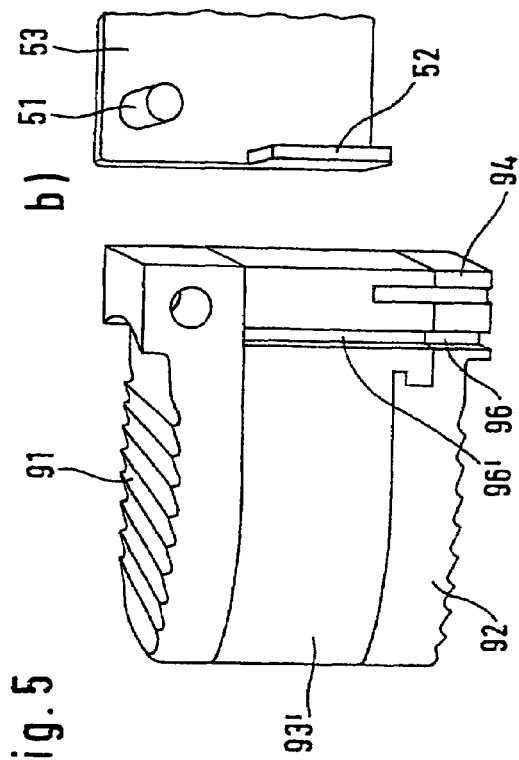
FIG. 5 shows a detail view of the insertion instrument with an intervertebral endoprosthesis arranged thereon.
Figure 5:
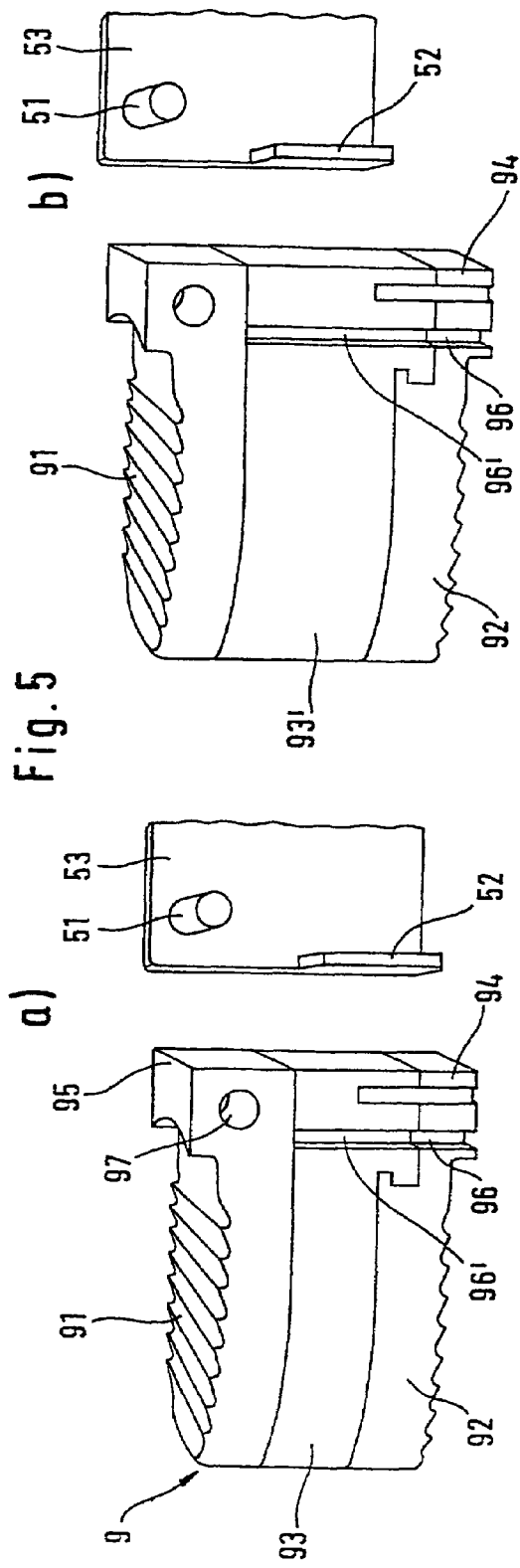

It is furthermore possible to implant cervical prostheses of different height without making changes to the forceps 1. FIG. 5 shows cervical prosthesis 9, 9', one of which has a thicker sliding core 93'. Like the sliding core 93, it is provided with a slit 96' which is flush with the slit 96 of the bottom closure plate 92. This configuration of the receiving opening on the bottom closure plate 92 as a slit 96 and its continuation as slit 96' in the sliding core 93' ensure that the thicker cervical prosthesis 9' can be gripped and securely held with the same forceps 1 without changing the arrangement of the projections 51, 52. The positioning precision is in this case guaranteed by the pin-like projections 51 which engage in the bores 97.

If necessary, however, it is also possible to provide other jaw inserts 53' which have a different arrangement of the projections 51', 52', as is shown in FIG. 4. In the example shown, the projections are closer together and are in one plane. In this way, the forceps 1 can be adapted to other intervertebral endoprostheses, for example to particularly small ones for treatment of children.

With its abutment surface 62, the block 61 affords a sufficiently large force transmission surface for transmitting to the cervical prosthesis 9 the impulses applied to the bulge 76 acting as the strike head. The great advantage of this is that the projections 51, 52, which have been finely dimensioned in the interest of precise positioning, do not have to transmit the strike forces, so that the risk of bending or even breaking of the projections 51, 52 as a result of overloading is excluded even when highly loaded through strikes, by virtue of the block 61, 61' and its abutment surface 62 assuming the role of force transmission.

The forceps 1 according to the invention allows the cervical prosthesis 9 to be arranged with precise positioning and without any risk of it being the wrong way round on the forceps 1, thereby preventing any undesired opening of the cervical prosthesis 9. Moreover, by virtue of the block 61, 61' with abutment surface 62, it also permits transmission of forces even in the case of forceps 1 of small dimensions. In this way, reliable implantation of the prosthesis is guaranteed. The small dimensioning also has the advantage that it gives the operating surgeon good access to and a good overall view of the implantation site.

The invention claimed is:

1. A multi-part intervertebral endoprosthesis system, comprising:
   a multi-part intervertebral endoprosthesis, comprising,
     a top closure plate,
     a bottom closure plate, and
     a sliding core between the top and bottom closure plates, each closure plate including a pair of receiving openings, and
   an insertion instrument which comprises a handgrip and a gripping portion for engaging the top and bottom closure plates with corresponding retention projections which, in order to hold the intervertebral endoprosthesis on the insertion instrument, are configured to engage with the corresponding receiving openings,
   the receiving openings being arranged in lateral side faces relative to an implanted position of the closure plates, and the receiving openings assigned to one of the closure plates each have an elongate shape extending in a direction toward the other closure plate.

2. The multi-part intervertebral endoprosthesis system of claim 1, wherein the receiving openings with an elongate shape are in the form of a slit.

3. The multi-part intervertebral endoprosthesis system of claim 1 or 2, wherein the receiving openings with an elongate shape extend over the entire height of the closure plate.

4. The multi-part intervertebral endoprosthesis system of claim 1 or 2, wherein the receiving openings with an elongate shape extend over part of the height of the sliding core.

5. The multi-part intervertebral endoprosthesis system of claim 1 or 2, wherein the receiving openings with an elongate shape extend over the entire height of the sliding core.

6. The multi-part intervertebral endoprosthesis system of claim 1 or 2, wherein the receiving openings with an elongate shape narrow with increasing depth relative to a height of the multi-part intervertebral endoprosthesis.

7. The multi-part intervertebral endoprosthesis system of claim 1 or 2, wherein receiving openings assigned to the other closure plate have a round shape.

8. The multi-part intervertebral endoprosthesis system of claim 1 or 2, wherein the retention projections are plates or pins.

9. A kit, comprising:
   the multi-part intervertebral endoprosthesis system of claim 1 or 2,
   and further comprising different sizes of sliding cores of different thicknesses.

10. The multi-part intervertebral endoprosthesis system of claim 1, wherein the gripping portion of the insertion instrument comprises a block with an abutment surface configured for bearing on the at least one of the closure plates, said block being connected to a force-receiving part on the insertion instrument for applying an insertion force to the intervertebral endoprosthesis.

11. The multi-part intervertebral endoprosthesis system of claim 10, wherein the block is arranged rigidly on the gripping portion.

12. The multi-part intervertebral endoprosthesis system of claim 11, wherein the block is secured to the gripping portion with a through-screw.

13. The multi-part intervertebral endoprosthesis system of claim 11, wherein the block is secured to the gripping portion with a clamping screw.

14. The multi-part intervertebral endoprosthesis of claim 11, 12 or 13, wherein the block is arranged on a jaw insert.

15. The multi-part intervertebral endoprosthesis system of claim 10, 11, 12 or 13, further comprising a rod with a handle in the rear area of the handgrip arranged on the block.

16. The multi-part intervertebral endoprosthesis system of claim 15, wherein the handle is designed as a strike head.

17. The multi-part intervertebral endoprosthesis of claim 16, wherein the block is arranged on a jaw insert.

* * * * *

UNITED STATES PATENT AND TRADEMARK OFFICE
CERTIFICATE OF CORRECTION

| | |
|---|---|
| PATENT NO. | : 7,320,689 B2 |
| APPLICATION NO. | : 10/619179 |
| DATED | : January 22, 2008 |
| INVENTOR(S) | : Arnold Keller |

It is certified that error appears in the above-identified patent and that said Letters Patent is hereby corrected as shown below:

In Column 6, line 3, please replace "5*a*shows" with --5*a* shows--

In Column 7, line 25, please replace "61'and" with --61' and--

In Column 8, line 34, please replace "rod. 71" with --rod 71--

Signed and Sealed this

Thirteenth Day of May, 2008

JON W. DUDAS
*Director of the United States Patent and Trademark Office*